United States Patent
Irion et al.

(12)
(10) Patent No.: US 6,648,816 B2
(45) Date of Patent: Nov. 18, 2003

(54) DEVICE FOR INTRACORPORAL, MINIMAL-INVASIVE TREATMENT OF A PATIENT

(75) Inventors: Klaus M. Irion, Liptingen (DE); Peter Schwarz, Tuttlingen (DE); Mark Kocher, Sindelfingen (DE)

(73) Assignee: Karl Storz GmbH & Co. KG (DE)

( * ) Notice: Subject to any disclaimer, the term of this patent is extended or adjusted under 35 U.S.C. 154(b) by 82 days.

(21) Appl. No.: 09/968,195

(22) Filed: Oct. 1, 2001

(65) Prior Publication Data

US 2002/0049367 A1 Apr. 25, 2002

Related U.S. Application Data

(63) Continuation of application No. PCT/EP01/01039, filed on Jan. 31, 2001.

(30) Foreign Application Priority Data

Feb. 1, 2000 (DE) .......................................... 100 04 264

(51) Int. Cl.[7] ................................................. A61B 1/05
(52) U.S. Cl. ........................ 600/173; 600/106; 600/104
(58) Field of Search ................................ 600/104, 173, 600/106, 129, 111, 166, 109; 348/65, 66

(56) References Cited

U.S. PATENT DOCUMENTS

| | | | | |
|---|---|---|---|---|
| 4,633,304 A | * | 12/1986 | Nagasaki ..................... | 348/69 |
| 4,915,626 A | * | 4/1990 | Lemmey ..................... | 433/31 |
| 5,166,787 A | | 11/1992 | Irion .......................... | 358/98 |
| 5,305,121 A | * | 4/1994 | Moll ........................... | 348/45 |
| 5,368,015 A | | 11/1994 | Wilk ........................... | 128/4 |
| 5,408,409 A | | 4/1995 | Glassman et al. ..... | 364/413.13 |
| 5,653,677 A | * | 8/1997 | Okada et al. ............... | 600/112 |
| 5,797,835 A | * | 8/1998 | Green ......................... | 600/106 |
| 5,825,982 A | | 10/1998 | Wright et al. ............... | 395/94 |
| 5,836,869 A | * | 11/1998 | Kudo et al. ................. | 600/173 |
| 6,066,090 A | * | 5/2000 | Yoon ........................... | 600/113 |
| 6,117,071 A | * | 9/2000 | Ito et al. ..................... | 600/168 |
| 6,277,064 B1 | * | 8/2001 | Yoon ........................... | 600/114 |
| 6,309,345 B1 | * | 10/2001 | Stelzer et al. ............... | 600/106 |

FOREIGN PATENT DOCUMENTS

| | | |
|---|---|---|
| DE | 39 21 233 A1 | 2/1991 |
| DE | 195 29 950 C1 | 8/1995 |
| JP | 5115425 * | 5/1993 |
| JP | 09028663 | 4/1997 |
| WO | WO98/46120 | 4/1998 |

* cited by examiner

Primary Examiner—John P. Leubecker
(74) Attorney, Agent, or Firm—St. Onge Steward Johnston & Reens LLC

(57) ABSTRACT

The present invention describes a device for intracorporal, minimal-invasive treatment of a patient, comprising a working instrument that can be introduced into a body cavity of the patient for carrying out a treatment step, wherein a distal end of the introduced working instrument defines an intracorporal working area, and at least one image pick-up unit for picking up an image of the intracorporal working area, further comprising positioning means for orienting an optical axis of the image pick-up unit in dependency on a spatial position of the intracorporal working area, wherein the positioning means comprise a guide shaft, in which the working instrument is guided, and wherein the image pick-up unit is pivotably fixed at an intracorporal portion of the guide shaft. The positioning means have a holder pivotably fixed to the intracorporal portion of the guide shaft, the image pick-up unit being arranged at the holder in a distance from a location where the holder is linked to the guide shaft, such that the image pick-up unit is intracorporally pivotable into a working position, in which the optical axis runs angularly to a longitudinal center axis of the guide shaft and points to the longitudinal center axis.

29 Claims, 6 Drawing Sheets

DEVICE FOR INTRACORPORAL, MINIMAL-INVASIVE TREATMENT OF A PATIENT

CROSS REFERENCE TO PENDING APPLICATION

The present application is a continuation of pending International Patent Application PCT/EP01/01039 filed on Jan. 31, 2001, which designates the United States and claims priority of German Patent Application 100 04 264 filed on Feb. 1, 2000.

BACKGROUND OF THE INVENTION

The present invention relates to a device for intracorporal, minimal-invasive treatment of a patient, comprising a working instrument that can be introduced into a body cavity of the patient for carrying out a treatment step, wherein a distal end of the introduced working instrument defines an intracorporal working area, and at least one image pick-up unit for picking up an image of the intracorporal working area, further comprising positioning means for orienting an optical axis of the image pick-up unit in dependency on a spatial position of the intracorporal working area, wherein the positioning means comprise a guide shaft, in which the working instrument is guided, and wherein the image pick-up unit is pivotably fixed at an intracorporal portion of the guide shaft.

Such a device is known from U.S. Pat. No. 5,166,787.

In the minimal-invasive, surgical treatment of patients, working instruments are brought to the location to be treated in the body of the patient merely through one or several small incisions. The visual control of the working steps to be carried out in the body of the patient is done endoscopically. An example for a minimal-invasive standard operation is the laparoscopical colecystectomy. In this procedure, three small openings are cut into the abdominal area of the patient. One of the openings serves for introducing an endoscope with a video camera, the image of which can be seen on a monitor by the treating physician. Working instruments, like e.g. scissors, forceps or the like, are introduced through the other two openings.

When the operation is carried out, the endoscope is, today, usually handled by an assistant physician, who tracks the endoscope to changes and displacements of the working area so far that the treating physician always has the working instruments in his visual field. Such camera assistance requires, however, a very good coordination between the treating physician and the assistant physician, what often is problematic in practice. Moreover, the necessary camera assistance requires more staff in carrying out the operation, which has a negative effect on the costs.

In DE 195 29 950 C1, a device was, thus, suggested, in which the camera assistant is replaced by an automatically controlled robot that is arranged outside the body of the patient. For the control of the robot, the image picked up by the endoscope camera is evaluated with reference to the position of working instrument or instruments appearing in the image picked up. The working instruments are marked with colors to this end, so that they can be identified by means of the proposed image treatment algorithm.

It is true that such a robot control can generally replace the assistant physician required as in the past, it is, however, expensive from the technical point of view and has, moreover, further disadvantages. In particular, the robot system requires a very large mechanical holder, which takes a relatively large space over the patient. This limits the freedom of movement for the treating physician over the patient. Apart from that, the sterilization of the relatively large robot device is difficult. The assembly and disassembly of such a device also requires relatively much time, what has a negative effect on the costs and the efficiency particularly in standard operations.

From U.S. Pat. No. 5,166,787 mentioned at the outset, an endoscope with a video camera arranged on its distal end is known, wherein the video camera is movable as a whole with respect to the distal end of the endoscope shaft after being introduced into the body cavity to be examined of the patient. The video camera can be pivoted about an axis running parallel with respect to the longitudinal axis of the shaft, which forms a body-own axis of the video camera, in a plane transverse to the longitudinal direction of the shaft out of the longitudinal axis of the shaft. The viewing direction of the video camera remains, in this procedure, in every pivot position of the video camera parallel with respect to the longitudinal center axis of the shaft. In another embodiment, the video camera is additionally pivotable, about a pivot axis running transversely with respect to the longitudinal direction of the shaft, again, about a video camera-own axis. In this procedure, the viewing angle of the video camera is changed with respect to the longitudinal axis of the shaft, however, only such viewing directions are created, which form a very acute angle with the longitudinal axis of the shaft, or such viewing directions, which are facing away from the longitudinal center axis of the shaft and are, thus, not useful for the endoscope when used in an operation. In other words, it is not possible to reach the same or at least similar perspective observation conditions with this known endoscope as with an endoscope that was introduced into the body cavity via an additional access.

Neither the known endoscope nor the video camera, moreover, have positioning means by which the viewing direction and/or the image field of the video camera can automatically be tracked to certain displacements or shiftings of the intracorporal working area. Thus, also for this known device a manual positioning with the disadvantages already mentioned is necessary.

It is, thus, an object of the present invention to provide a device of the type mentioned at the outset, by which at least similar perspective viewing conditions can be reached like with an endoscope that is introduced into the body cavity via an additional access.

SUMMARY OF THE INVENTION

According to the invention, the object underlying the invention is achieved by a device for intracorporal, minimal-invasive treatment of a patient, comprising:

a working instrument that can be introduced into a body cavity of said patient for carrying out a treatment step, said working instrument having a distal end defining an intracorporal working area when said working instrument is introduced in said body cavity;

at least one image pick-up unit for picking up an image of said intracorporal working area, said image pick-up unit having an optical axis; and positioning means for orienting said optical axis of said image pick-up unit in dependency on a spatial position of said intracorporal working area, said positioning means further comprising:

a guide shaft in which said working instrument is guided, said guide shaft having an intracorporal portion, and a holder pivotably fixed to said intracorporal portion of said guide shaft, wherein said image pick-up unit is arranged at said holder in a distance from a location where said holder is linked to said guide shaft, such that said image pick-up unit is intracorporally pivotable into a working position, in which said optical axis runs angularly to a longitudinal center axis of said guide shaft and points to said longitudinal center axis.

The device according to the invention differs from the known device in particular by the fact that the image pick-up unit is fixed at the guide shaft via a holder, and, due to the pivotability of the holder, can be pivoted away from the guide shaft, i.e. can be spaced apart from the guide shaft. In that way, the viewing direction can be positioned under a larger angle with respect to the longitudinal axis of the guide shaft, which corresponds to the perspective viewing conditions of an endoscope being introduced through an additional opening into the body cavity, what is welcomed by the physician. By the coupling of the image pick-up unit with the intracorporal portion of the guide shaft, it is moreover possible, as is in the following described in more detail, that the image pick-up unit can automatically follow at least a part of the movements of the working instrument, without a robot or a corresponding device outside of the body cavity being necessary. It is therefore practically a seeing working instrument. The device according to the invention is consequently considerably smaller and more space saving and less cost-expensive than common devices with an extracorporal positioning device.

By means of the present invention, practically a "distal end of an endoscope" is coupled with the working instrument, which can be positioned with a perspective viewing direction onto the working area, just as if a whole endoscope was introduced into the body cavity through an additional opening.

In preferred embodiments of the invention, which are described in more detail in the following, a separate holder for the image pick-up unit outside the body cavity of the patient can even be completely omitted, so that in this case no additional space at all over the patient is necessary. The freedom of movement for the treating physician is then not limited at all anymore.

In addition, with the smaller device the effort for assembly and disassembly is reduced, what has a positive effect on the efficiency and the handling in practical use.

Finally, the sterilization of the device according to the invention is easier due to the smaller dimensions. In spite of all that, the device of the invention has all advantages of an automatic tracking system, so that, altogether, a considerable cost saving in minimal-invasive treatments of patients is possible. Apart from that, the risk of an unintended contamination of the image pick-up unit by tissue contact is reduced. Furthermore, also shorter operation times can be reached due to the improved handling, what results in less strain and a lesser operation risk for the patient.

In minimal-invasive operations, as already mentioned at the outset, two incisions are created, wherein an active working element, e.g. scissors is introduced, through the first incision, from the sight of the physician usually the "right" one, and, a passive or more passive working instrument, e.g. a holding instrument, is introduced through the other one, i.e. from the sight of the physician the "left" one. For the device according to the invention, it is particularly preferred in this sense, if the image pick-up unit is coupled with the more passive working instrument via the guide shaft.

The object mentioned before is therefore completely achieved.

In a preferred embodiment, the holder has at least one pivot arm that is articulatedly fixed to the intracorporal portion.

By this measure, the device with the functions and effects according to the invention mentioned before can be configured particularly simple in design in order to configure a coupling of the image pick-up unit on the guide shaft for obtaining perspective viewing conditions.

In a particularly simple preferred embodiment, the image pick-up unit is arranged at the free end of the at least one pivot arm in such a way that the optical axis of the image pick-up unit runs approximately perpendicular to the longitudinal axis of the pivot arm and points to the longitudinal center axis of the guide shaft.

In this embodiment, only one articulation is necessary in an advantageous manner, namely the one via which the at least one pivot arm is connected to the guide shaft and via which the image pick-up unit can then be pivoted out from the guide shaft for adjusting a perspective viewing angle, in order to adjust the desired perspective angle between the longitudinal axis of the guide shaft or the working instrument and the image pick-up unit.

In such a simple embodiment of the device according to the invention, it is advantageous to integrate even more than one image pick-up unit in order to obtain a video stereo system for an improved stereoscopic representation and reproduction.

In the embodiment mentioned before, it is further preferred if the pivot arm has an adjustable length.

This measure has the advantage that in a displacement of the working instrument in axial direction the angle between the optical axis and the image pick-up unit and the longitudinal axis of the working instrument can be held constant by shortening or extending the pivot arm in the one-axis embodiment of the articulation mechanism. The pivot arm can be designed in a telescope-like manner to this end, for example.

In another preferred embodiment of the invention, the holder has a one-axis or a multi-axis articulation mechanism.

This measure has the advantage that with increasing number of the axes of the articulation mechanism the number of degrees of freedom of movement of the image pick-up unit increases with reference to the guide shaft. As a result, the image pick-up unit can be oriented onto the working area, if a multi-axis articulation mechanism is used.

In another preferred embodiment, the image pick-up unit is pivotable into a resting position at the guide shaft, in which an outer cross-sectional contour of the image pick-up unit is arranged in an essentially congruent manner with respect to an outer cross-sectional contour of the guide shaft.

This measure has the advantage that the image pick-up unit can be introduced together with the guide shaft, i.e. through the same opening, into the body cavity of the patient. As a result, e.g. in laparoscopical colecystectomy, one of the three incisions required up to now can be dispensed with. This results in a lesser traumatization of the patient, what results, again, in a lesser risk. In other applications, e.g. in tube sterilization, even only one incision is required with the perspectively seeing instrument of the invention.

In another embodiment of the invention, the image pick-up unit is fixable via an intracorporally activatable coupling mechanism at the guide shaft.

In this embodiment of the invention, the initially separate image pick-up unit can be intracorporally fixed at the guide shaft. By this measure, it is possible to introduce the image pick-up unit separately from the guide shaft into the body cavity of the patient, e.g. over an own incision opening. The measure has the advantage that both the image pick-up unit and the guide shaft each for itself can be realized in a larger dimension, so that altogether there is more construction space available. This is particularly advantageous in view of the image pick-up unit, since a larger construction space can, for example, receive more optical fibers and, thus, allows a higher light intensity.

In another embodiment of the invention, the positioning means comprise a mechanically constrained coupling between the working instrument and the image pick-up unit.

A mechanically constrained coupling allows in a simple way an automatic tracking of the image pick-up unit, without additional actuating drives or sensors being necessary. As a result, this embodiment of the invention can be realized with very low costs and, moreover, in a very robust manner. The latter is particularly advantageous for the practical use in working and in sterilizing.

In this connection, it is preferred if the positioning means have locking means for an at least partial axial immobilization of the working instrument with respect to the guide shaft.

This measure represents the simplest tracking between the image pick-up system and the working area, as the image pick-up unit connected with the guide shaft via the holder, by the axial fixation of the working instrument with respect to the guide shaft, is entrained by every axial movement of the working instrument. The pivoted position of the holder is maintained in the simplest case, so that also the perspective viewing direction remains unchanged. The perspective observation angle can, before, be fixed by pivoting the holder and, thus, the image pick-up unit, such that the point of the working instrument which defines the working area rests approximately in the image center. The working instrument is then immobilized e.g. at the proximal side at the guide shaft by means of the locking means, such that it is preferably rotationally movable in the guide shaft, but can, however, be axially moved only in connection with the guide shaft. In order to achieve a complete axial fixation of the working instrument at the guide shaft, in the simplest case, an annular groove can be provided in the guide shaft in which runs a pin which is preferably spring-loaded and which is located at the working instrument. By such a locking, it is guaranteed that the working area lies in the viewing area of the image pick-up unit in spite of a movement of the working instrument.

In this connection, it is further preferred if the locking means are configured in such a way that the working instrument is axially freely displaceable with respect to the guide shaft within predetermined limits, but axially entrains the guide shaft, if the working instrument is displaced beyond the predetermined axial limits.

It may be interfering when the image pick-up unit always follows the working instrument when it is axially moved, so that no visual registration of the movement of the instrument is possible. By the embodiment described before, it is now possible to move the instrument axially with respect to the guide shaft within predetermined limits, without the guide shaft and, with it, the image pick-up unit being also moved. The limits mentioned before are preferably adjusted in such a way that they just correspond to the distance between the entering of the point of the working instrument into the image field and the outgoing of the point of the working instrument from the image field. Only if the point of the working instrument would leave the image field, the locking means become active and entrain, then, the guide shaft and, with it, the image pick-up unit. Such locking means may be realized by a broader annular groove in the guide shaft, in which runs a pin arranged at the working instrument which is axially shorter compared to the axial length of the annular groove.

In comparison to the very simple tracking mentioned before, it is also preferred if the working instrument is axially freely displaceable with respect to the guide shaft, and that the holder has coupling means, which can be brought in engagement with the working instrument in such a way that, when the working instrument is displaced relative to the guide shaft, the holder is pivoted, in order to track the optical axis to the working area.

In this embodiment, thus, an axial relative displacement between the working instrument and the guide shaft results in a pivoting of the holder at the guide shaft and, thus, in a change of the viewing direction of the image pick-up unit, wherein the coupling causes the viewing direction of the image pick-up unit to be always directed onto the working area.

In a further embodiment of the invention, the positioning means comprise an actuator unit for pivoting the image pick-up unit and a sensor unit coupled therewith, by which a current position of the working area can be determined.

This measure may be used alternatively to a mechanically constrained coupling. The measure is, however, preferably used complementary to a mechanically constrained coupling, wherein the mechanically constrained coupling on the one hand and the sensor/actuator unit on the other hand control different degrees of freedom of movement of the image pick-up unit. The measure has the advantage that a sensor/actuator unit allows an electronic positioning, which results in a higher flexibility and a larger scope of arrangements. This holds true both for the design of the device according to the invention and for its practical use.

In a further embodiment of the measure mentioned before, the sensor unit comprises measuring means for determining a relative position of the working instrument with reference to the guide shaft.

The measuring means may e.g. comprise a bar code, a resistance measurement, an angle decoder or a position sensor on the basis of infrared, ultrasound or electromagnetic fields. The measure has the advantage that such position sensors are sufficiently known per se in the prior art, so that a position determination by a position sensor is very simply possible. The reference to the guide shaft allows, moreover, a reference that is always constant and exactly known.

In a further embodiment, which can be used both alternatively and complementary to the measure mentioned before, the sensor unit comprises image-processing means for identification of the distal end of the working instrument in the image picked up.

This measure has the advantage that additional measuring devices, like e.g. in the form of a position sensor, can be dispensed with, whereby the necessary construction space can also be saved. Complementary to a position sensor, a redundancy is achieved which allows an increase of the reliability and measuring accuracy.

Preferably, in the working position, the optical axis encloses an angle of at least 10°, particularly preferably between 20° and 700°, with the longitudinal center axis of the guide shaft.

Also preferably, in the working position, the image-entering opening of the image pick-up unit is in a lateral distance from the guide shaft, which is larger than approximately 1 cm.

Due to these measures, the operating physician achieves an optimal viewing angle onto the working area, what considerably facilitates the carrying out of the operation. From an angle of about 10°, the operating physician achieves a sufficient lateral view (perspective) on the distal end of the working instrument. The angle range between 20° and 70° is optimal. The measure is particularly advantageous if the image pick-up unit is introduced via the same incision into the body cavity of the patient as the guide shaft, as the operating physician would otherwise have to accept disadvantages with respect to the viewing angle in this case.

In a further embodiment of the invention, the image pick-up unit is an integrated video probe, which provides an electrical image signal of the working area.

Preferably, the video probe is a stereo video probe, which allows for the operating physician an, again, better perspective stereoscopic image, in particular in connection with the embodiment according to claim 3. The measure has generally the advantage that an electric image signal, in particular in digital form, can be transported without or with relatively slight quality losses, because no illustration errors like in lens systems occur. As a result, the quality of the image reproduction is very high in this measure. Just for stereo image pick-up units, the invention has the additional advantage that double images and/or distortion are reduced, as an always constant, optimal working distance and, thus, a constant 3D perspective are maintained.

In connection with the measure mentioned before, it is preferred if the image picked up by the image pick-up unit is telemetrically transmitted.

It is advantageous herewith that the image picked up by the video sensor can be transmitted into the proximal direction without expensive cable systems. In connection with the one-axis or multi-axis articulation mechanism mentioned before for coupling the image pick-up unit onto the guide shaft, this is particularly advantageous, because no cables have to be led through the articulation or the articulations of the pivot mechanism. Also the susceptibility for damages and an untightness due to the implementation of cables is considerably reduced by the measure mentioned before.

It is further preferred if the image pick-up unit has a transmitter, the transmitted image signals of which are received by a receiver.

The integration of a transmitter into the image pick-up unit, i.e. into the video sensor, has the advantage that cables for image transmission between the video sensor and the receiver can be completely dispensed with, so that the image pick-up unit can be completely encapsulated, wherein problems of tightness can be completely removed.

It is further preferred if the receiver or at least its antenna is arranged at the intracorporal portion of the guide shaft.

While it is also possible to do the telemetric transmission from the image pick-up unit through the abdominal wall to an extracorporally arranged receiver, the measure mentioned before has the advantage that also frequency ranges of higher frequency can be used, which, otherwise, would be dampened by the abdominal wall.

In a further preferred embodiment, an illuminating device is arranged at the image pick-up unit, which has preferably at least one light emitting diode.

This has the advantage that also for a light supply to the working area, optical fibers can be completely dispensed with, which cannot be led over the articulation mechanism and, thus, would have to be led through the guide shaft. A light emitting diode at the image pick-up unit has, however, the essential advantage that the direction of the illumination and the viewing direction of the image pick-up is the same, so that, when the image pick-up unit is tracked to a movement of the working instrument, also the illumination is optimally tracked.

In a further preferred embodiment, the image pick-up unit has a source of energy, e.g. a battery or an accumulator, for its supply.

Altogether, thus, a completely autonomous image pickup unit is created, if necessary, with a light source for illuminating the working area, the image pick-up unit being advantageous in connection with the positionability of the image pick-up unit according to the invention.

Taking CMOS video sensors as a basis, it is possible in the future that such autonomous image pick-up units can be manufactured as one-way products, so that problems of cleaning and recycling will not arise any more.

In an alternative embodiment of the measure mentioned before, the image pick-up unit is an optical element, which provides an optical image signal of the working area.

The optical element can be, for example, an ordered fiber bundle, a lens system and/or a mirror system. The measure has the advantage that such passive elements can be realized in very small dimensions and with usual, controllable techniques. This is particularly advantageous if the image pick-up unit is to be introduced via the same opening into the body cavity of the patient as the guide shaft.

In a further embodiment of the invention, the guide shaft has a guide channel that is open on both ends for receiving and guiding exchangeable working instruments.

This measure allows the operating physician to use different working instruments in the same guide shaft, wherein the image pick-up unit can always be constantly directed onto the defined working area. As a result, the operating physician can orient very quickly and simply even if the working instrument is changed. Alternatively to this measure, however, it is also possible to couple the different working instruments each with an own guide shaft.

As already mentioned before, according to embodiments mentioned before, the working instrument is guided in the guide shaft movably in axial direction.

This measure has the advantage that the operating physician can manipulate the working instrument in the working area as usual and, in doing so, can perform e.g. cuts with scissors in the usual way.

In a further embodiment, the working instrument is immovable in radial direction in the guide shaft.

This measure has the advantage that the guide shaft directly follows radial movements of the working instrument, which is a particularly simple and effective constrained coupling. When the working instrument rotates in the guide shaft, the guide shaft is preferably not entrained, so that the viewing direction of the image pick-up unit remains unchanged, as is provided in another preferred embodiment.

In comparison to a complete radial fixation, it can, however, be advantageous, again, if the working instrument has a certain radial play with respect to the guide shaft, so that, in a lateral movement of the working instrument transverse with respect to the longitudinal axis of the working instrument, the image pick-up unit is not entrained within certain limits and the image field remains unchanged, and an entrainment occurs only if the movement exceeds the limits, as it was described before for the axial mobility.

In a further embodiment of the invention, the image pick-up unit has means for modification of a picked up image sector.

In particular, the image pick-up unit of this embodiment has a zoom objective, by which the image of the working area can be enlarged within predetermined limits, without changing the spatial distance between the image pick-up unit and the working area. In that way, the operating physician obtains a further possibility to adjust a visual range that is optimal for the performance of the treatment, to be more precise, without having to change the position of the working instrument.

In a further embodiment of the invention, an illuminating device is arranged on the intracorporal portion of the guide shaft.

This measure has also the advantage that the working area is well illuminated. In combination with the measure mentioned before, due to the different illumination directions, different shadows are created, which cause an increase of the depth indentation or of the stereo effect.

It is to be understood that the features mentioned above and those yet to be explained below can be used not only in the respective combinations indicated, but also in other combinations or in isolation, without leaving the scope of the present invention.

BRIEF DESCRIPTION OF THE DRAWINGS

Embodiments of the invention are shown in the drawings and will be explained in more detail in the description below. In the drawings.

DETAILED DESCRIPTION OF PREFERRED EMBODIMENTS

Figure 1:
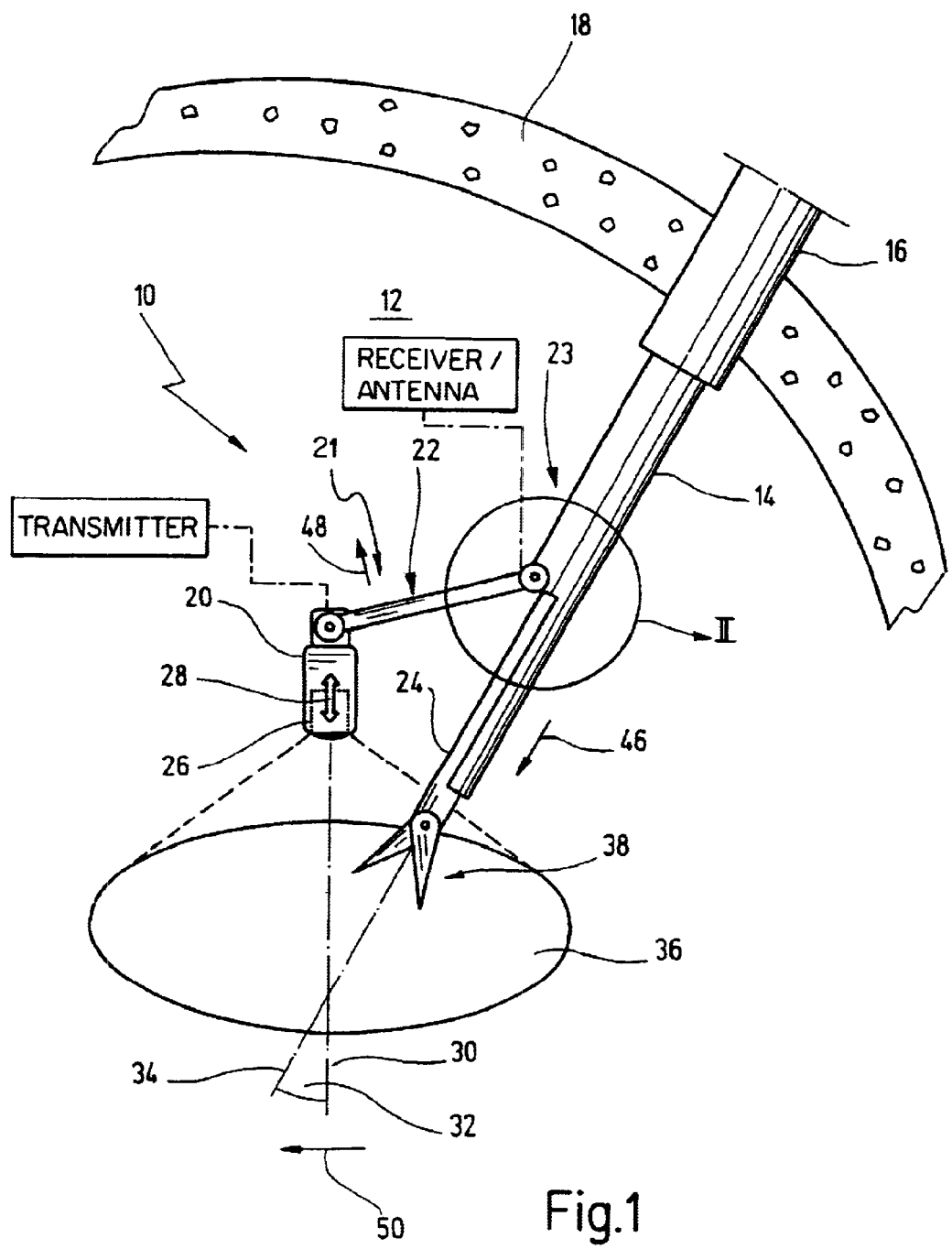
FIG. 1 shows a first embodiment of a device according to the invention.

In FIG. 1, a device according to the invention is altogether designated with the reference numeral 10. The device 10 serves for the performance of an operation in the abdomen 12 of a patient.

Device 10 comprises a guide shaft 14, which is introduced via a trocar 16 through the abdominal wall 18 of the patient into the abdomen 12. Alternatively, guide shaft 14 can also be part of trocar 16.

An image pick-up unit is designated with the reference numeral 20, which is fixed via a holder 21 at an intracorporal portion 23 of guide shaft 14, holder 21 having a multi-axis articulation mechanism 22, which has two articulation axes in the present case. The image pick-up unit is in this case an integrated, miniaturized video probe, which supplies an electrical image signal to an image reproduction unit being arranged outside abdomen 12 via an electrical connection not shown.

The image pick-up unit or video probe 20 can advantageously also have a transmitter, in order to transmit telemetrically the image taken by video sensor 20 in the form of transmitted image signals. For receiving these image signals, a receiver is arranged at intracorporal portion 23 of guide shaft 14.

A working instrument, which is in the present case a grasping forceps as an example, is designated with the reference numeral 24. Generally, working instrument 24 can be any instrument, which is required for the performance of the minimal-invasive operation in abdomen 12 of the patient.

Video probe 20 has in the present embodiment a zoom objective 26 with a variable focal distance, which is indicated by an arrow 28.

The optical axis of video probe 20 is designated with the reference numeral 30, the optical axis running in the working position shown under an angle 32 with respect to the longitudinal center axis 34 of guide shaft 14.

The working area of working instrument 24 is designated with the reference numeral 36, the working area being defined by the distal end 38 of working instrument 24.

Video probe 20 is connected in such a way with intracorporal portion 23 of guide shaft 14, via articulation mechanism 22 and via measures shown in more detail in the following, that its optical axis 30 and, thus, its viewing angle can always follow automatically spatial changes of working area 36. In order to explain this function, reference is additionally made to FIG. 2 in the following. The same elements as in FIG. 1 are designated with the same reference numerals.

Figure 2:
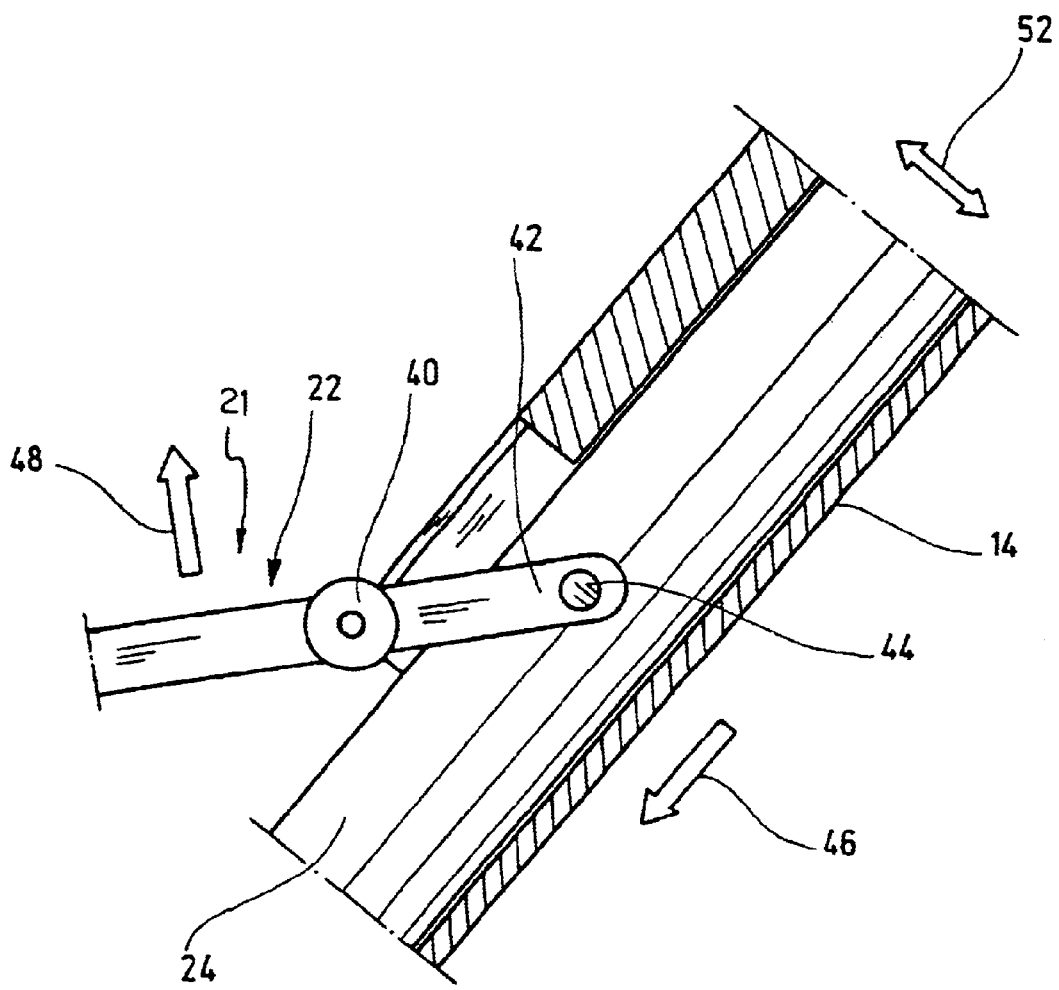
FIG. 2 shows an enlarged and partly sectioned portion of the device according to FIG. 1.

As can be seen in FIG. 2, articulation mechanism 22 is fixed at guide shaft 14 via an articulation 40, wherein articulation 40 is the point where holder 21 is linked to guide shaft 14. Image pick-up unit 20 is arranged at holder 21 in a distance from this link, in the embodiment shown at the outer free end. Articulation mechanism 22 has a lever arm 42, which projects into the inner part of guide shaft 14 via articulation 40. At the free end of lever arm 14, a spring-loaded sphere 44 is shown, which is an example for a locking mechanism not described in detail.

Working instrument 24 is releasably connected with lever arm 42 via sphere 44 or via the locking mechanism represented more generally thereby. This connection has as result that a movement of working instrument 24 into the direction of an arrow 46, i.e. a movement in axial direction, tilts articulation mechanism 22 into the direction of an arrow 48. In that way, optical axis 30 of video probe 20 is moved into the direction of an arrow 50, so that the viewing angle of video probe 20 finally follows the axial movement of working instrument 24.

In a movement of working instrument 24 against the direction of arrow 46, the viewing angle of video probe 20 is displaced in reversed direction, so that video probe 20 altogether is automatically tracked to a displacement of working area 36, due to the mechanically constrained guiding via lever arm 42 and sphere 44.

In radial direction, i.e. in the direction of an arrow 52 in FIG. 2, working instrument 24 has no degree of freedom of movement with respect to guide shaft 14. As a result, guide shaft 14 follows every movement of working instrument 24 in the direction of arrow 52. As can easily be understood, by this measure, the viewing direction of video probe 20 is also tracked to a movement of working area 36. However, a certain radial play between the working instrument and guide shaft 14 may be provided, so that the tracking is only performed in movements of working instrument 24 which exceed the play.

An automatic tracking of image pick-up unit 20 with respect to axial movements of working instrument 24 can be omitted if the viewing field of image pick-up unit 20 is so wide that distal end 38 of working instrument 24 is always visible when being manipulated by the operating physician. This may be considered in device 10, for example, by the fact that working instrument 24 has, with respect to the free end of lever arm 42, a play, so that lever arm 42 follows movements of working instrument 24 not before a predetermined intensity.

In the following description of other embodiments, the same reference numerals further designate the same elements as in the previous figures.

Figure 3:
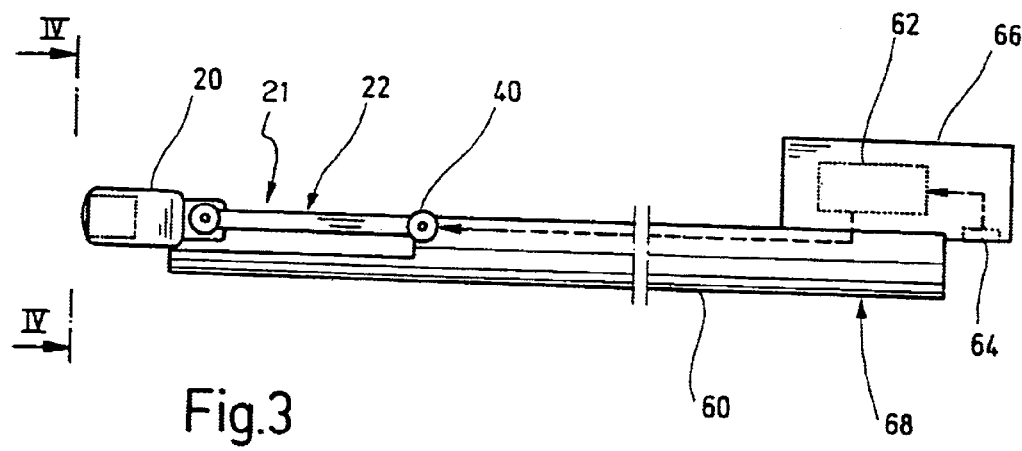
FIG. 3 shows a guide shaft with an image pick-up unit according to a second embodiment of the invention.

Guide shaft 60 in FIG. 3 differs from guide shaft 14 in the first embodiment essentially by an actuator unit 62 and a sensor unit 64 connected with same, which are arranged in a common housing 66 at the proximal end 68 of guide shaft 60. Actuator unit 62 comprises an evaluation unit not shown in detail and an actuating drive also not shown in detail, which controls holder 21 comprising articulation mechanism 22 and, thus, the adjustment of video probe 20. An intermittent motor is preferably used as actuating drive.

The sensor unit comprises in this embodiment a position sensor, which determines the relative position of working instrument 24 (here not shown) being guided in guide shaft 60 with respect to guide shaft 60. From the obtained position, the current position of working area 36 can be deduced, so that actuator unit 62 can track video probe 20 correspondingly.

In FIG. 3, video probe 20 is pivoted at guide shaft 60 in a resting position, which allows to introduce guide shaft 60 together with video probe 20 through trocar 16 into abdomen 12 of the patient to be treated. As can be seen in front view according to FIG. 4, video probe 20 is located in such a position that its outer cross-sectional contour 72 is arranged essentially within and, thus, congruent to the outer cross-sectional contour of guide shaft 60. The working position of video probe 20 of guide shaft 60 corresponds to the representation of guide shaft 14 in FIG. 1.

Figure 4:
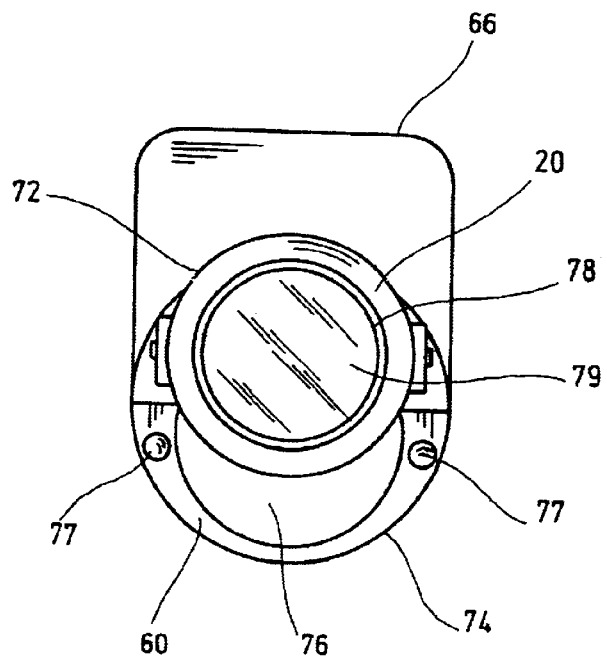
FIG. 4 shows the guide shaft in FIG. 3 along the line IV—IV.

In the representation in FIG. 4, furthermore, a guide channel 76 of guide shaft 60 can be seen, which is open on both ends, i.e. at its distal end 38 and at its proximal end 68. In that way, it is possible to introduce different working instruments 24 into guide shaft 60 or to remove them from the same in the course of the operation.

With reference numerals 77 and 78, two illumination devices are designated, which are arranged at the distal end of guide shaft 60 and at image pick-up unit 20. Illumination device 77 comprises two LED's, which are integrated in guide shaft 60 at both sides of guide channel 76. Illumination device 78 comprises, in comparison, a disordered fiber bundle, wherein the fiber ends are arranged concentrically to an image entrance opening 79. Instead of the fiber bundles, however, also LED's can be arranged at image pick-up unit 20. In the embodiment of the image pick-up unit described in connection with FIG. 1, for control and supply of the video probe and of the LED's mentioned before, furthermore, an energy source, e.g. a battery or an accumulator, can be provided in the image pick-up unit, so that the image pick-up unit works altogether autonomously.

Figure 5:
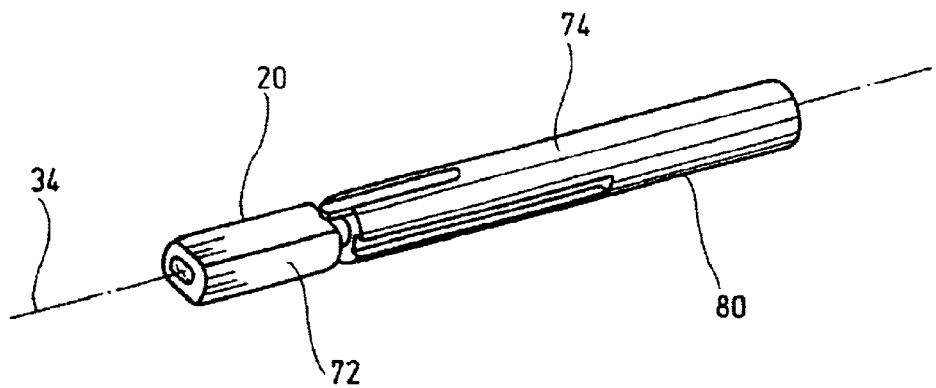
FIG. 5 shows a guide shaft with an image pick-up unit in resting position according to a third embodiment of the invention.
Figure 6:
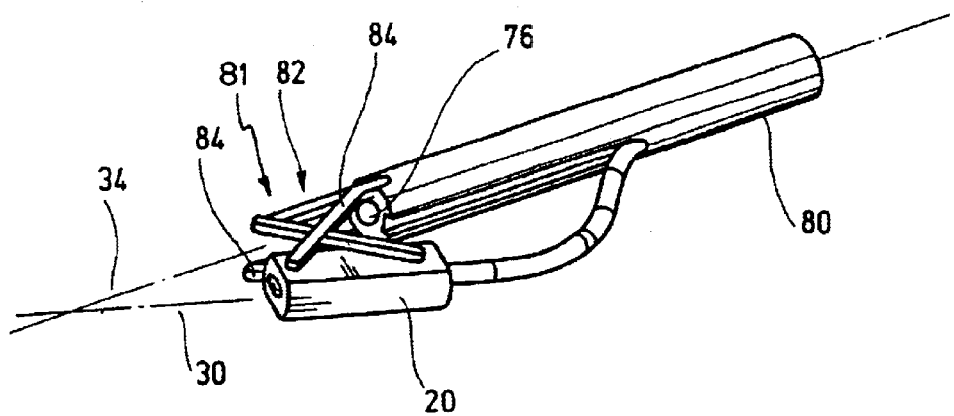
FIG. 6 shows the guide shaft from FIG. 5, wherein the image pick-up unit is pivoted in a working position.

In FIGS. 5 and 6, a further embodiment of a guide shaft according to the invention is designated with the reference numeral 80. The guide shaft 80 is connected to video probe 20 via a holder 81 having a multi-axis articulation mechanism 82. In its inner part, guide shaft 80 has a guide channel 76 open on both sides for receiving and guiding exchangeable working instruments 24.

Different from the previous embodiments, articulation mechanism 82 has in this embodiment two scissor-type members 84, between which video probe 20 is pivotably kept. As can be seen from the representation in FIG. 5, video probe 20 can also be pivoted into a resting position, in which its outer cross-sectional contour 72 is arranged within the outer cross-sectional contour 74 of guide shaft 80. In this case, outer cross-sectional contour 72 of video probe 20 is completely congruent to the outer cross-sectional contour 74 of guide shaft 80.

The functioning of guide shaft 80 corresponds to the one of the previous embodiments, wherein guide shaft 80 can be provided alternatively or complementary to each other both with a mechanically constrained coupling and with a sensor/actuator unit for tracking the video probe.

Figure 7:
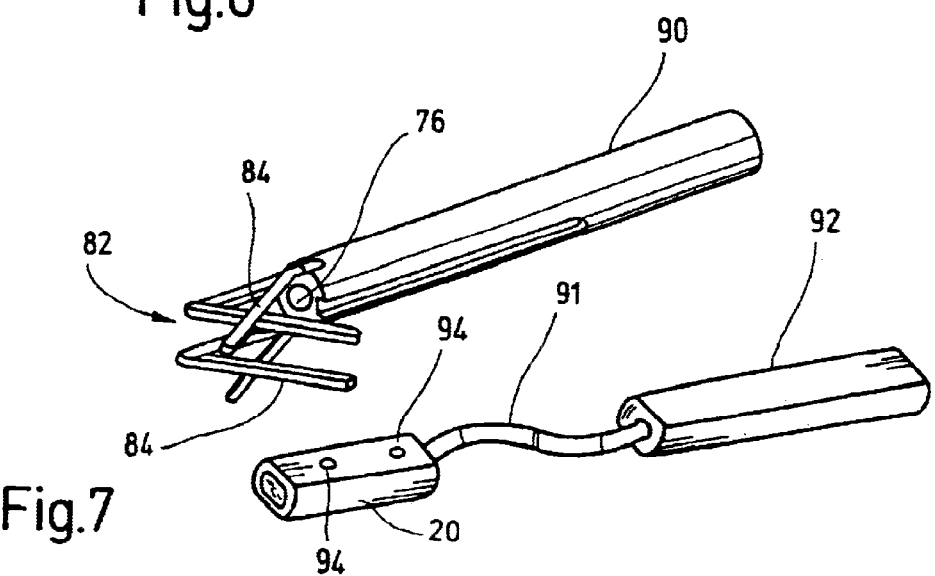
FIG. 7 shows a guide shaft and an image pick-up unit according to a second embodiment of the invention.

In FIG. 7, as a further embodiment of the invention, a guide shaft 90 is shown, which mainly corresponds to guide shaft 80 according to FIGS. 5 and 6. Different from that, video probe 20 can be separated, however, from articulation mechanism 82 and intracorporally coupled thereto. In that manner, it is possible to introduce video probe 20 and guide shaft 90 into abdomen 12 of a patient via different incisions. Video probe 20 is, in this procedure, connected with an own shaft 92 via a cable 91. The coupling of video probe 20 with articulation mechanism 82 is preferably performed by means of electromagnets 94, which are arranged at the outer side of video probe 20. The tracking of video probe 20 is done in the manner described before in this embodiment.

Figure 8:
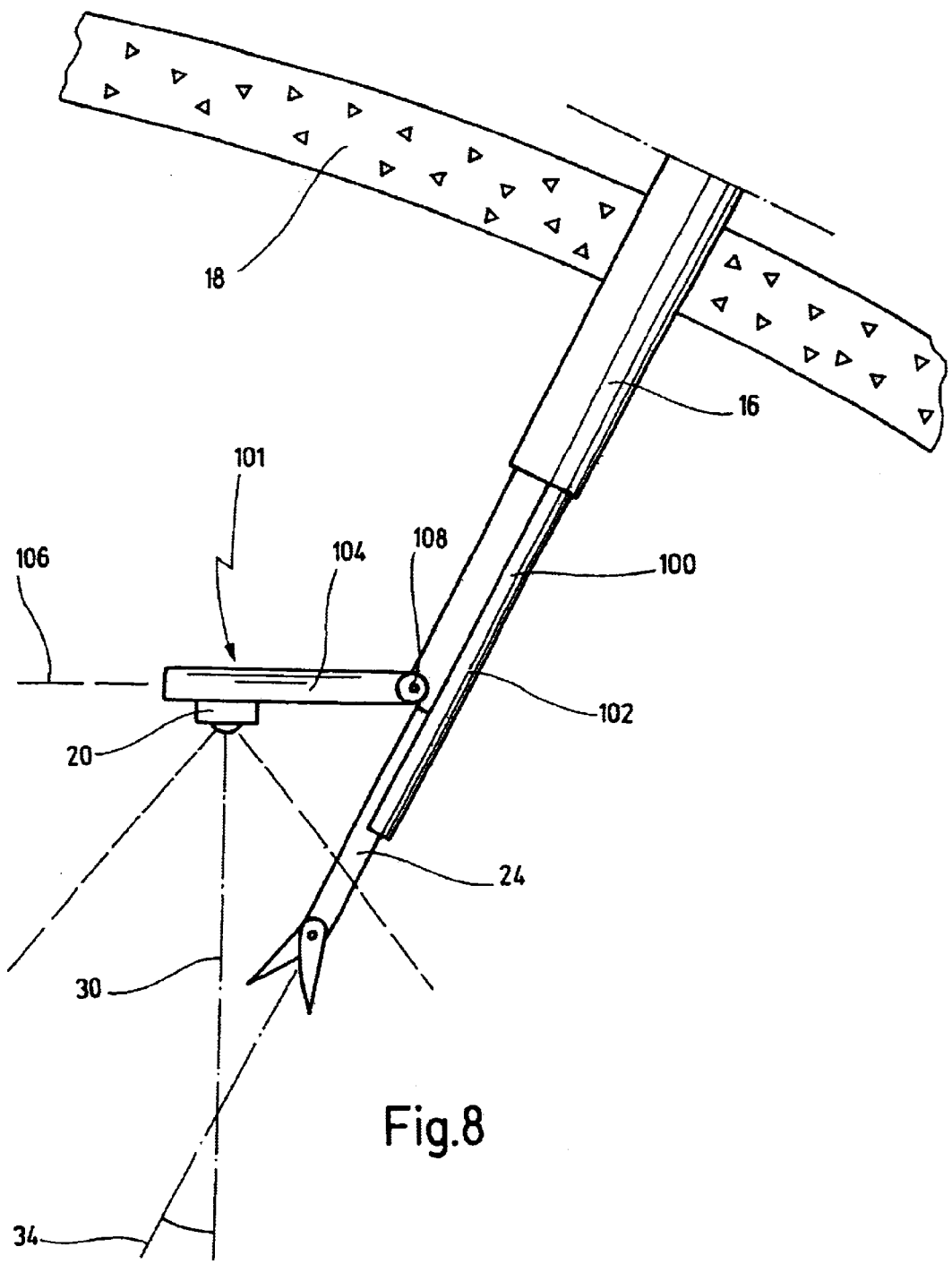
FIG. 8 shows another embodiment of a device according to the invention.
Figure 9:
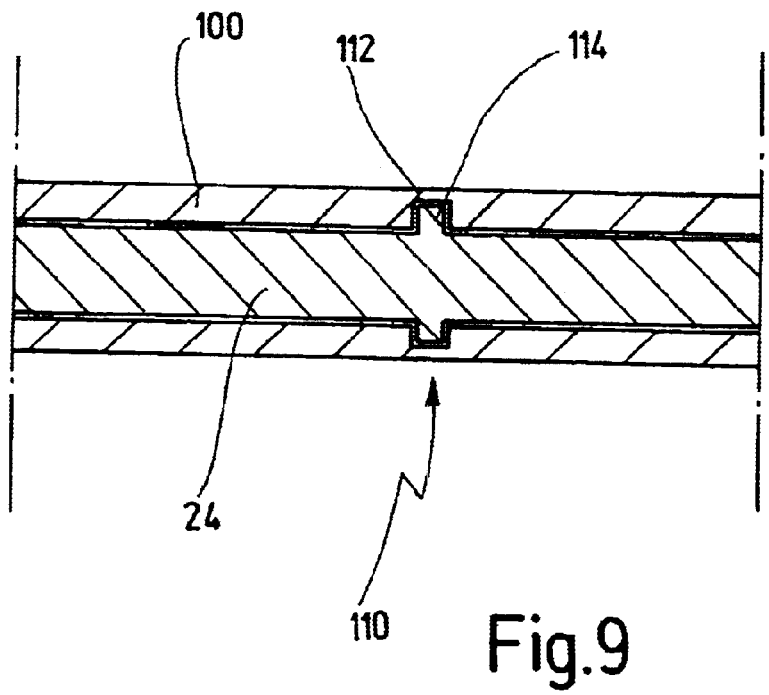
FIG. 9 shows a representation of a locking mechanism between a guide shaft of the device in FIG. 8 and a working instrument guided in same.
Figure 10:
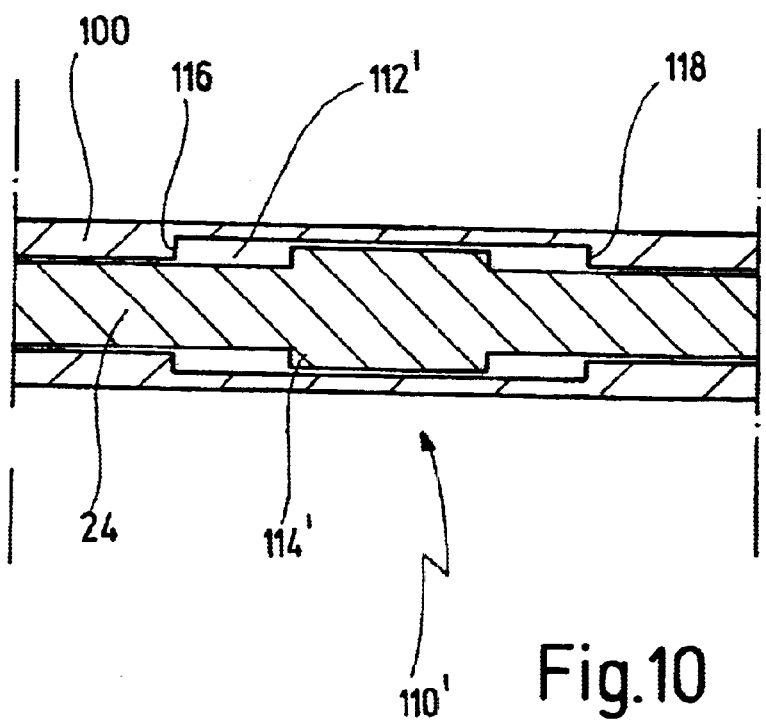
FIG. 10 shows an embodiment of a locking mechanism modified in comparison to FIG. 9 between a guide shaft of the device in FIG. 8 and a working instrument.

In FIGS. 8 through 10, as a further embodiment of the invention, a guide shaft 100 is shown, which is similar to guide shaft 14 according to FIGS. 1 and 2. The embodiment differs, however, according to FIGS. 8 through 10, by the coupling of image pick-up unit 20 onto guide shaft 100 and the type of tracking of image pick-up unit 20 with respect to working instrument 24.

Image pick-up unit 20 is fixed at guide shaft 100 via a holder 101, which has a pivot arm 104 articulatedly fixed at intracorporal portion 102 of guide shaft 100. Pivot arm 104 is, thus, a one-axis articulation mechanism for connection of image pick-up unit 20 with guide shaft 100.

Image pick-up unit 20 immovable with respect to pivot arm 104 is arranged in such a way at the free end of the at least one pivot arm 104 that optical axis 30 runs approximately perpendicular to longitudinal axis 106 of pivot arm 104 and points at the same time to longitudinal center axis 34 of guide shaft 100 or of working instrument 24.

Pivot arm 104 is pivotably connected to guide shaft 100 via an articulation 108, wherein the pivotability of pivot arm 104 like in the holders described before in connection with the other embodiments is such that optical axis 30 can enclose an angle of at least 10°, preferably of between 20° and 70°, with longitudinal center axis 34 of guide shaft 100, if the device is introduced into the body cavity.

In the working positions, image pick-up unit 20 is laterally spaced apart more than approximately 1 cm from guide shaft 100, with pivot arm 104 having a corresponding length to this end.

Furthermore, pivot arm 104 can be configured in telescope-like fashion, so that the length of pivot arm 104 and, thus, the distance of image pick-up unit 20 from the articulation point at guide shaft 100, which is formed by articulation 108, can be enlarged, so that the angle range mentioned before and the lateral distance can be maintained.

Whereas for holder 101 and, thus, for image pick-up unit 20, a mechanism comparable with FIG. 2 for tracking optical axis 30, i.e. the viewing direction of image pick-up unit 20 to a movement of working instrument 24, in particular an axial movement of working instrument 24, can also be provided in the embodiment in FIG. 8, now, a particularly simple tracking mechanism will be described with reference to FIGS. 9 and 10.

Instead of working instrument 24 being axially freely displaceable with respect to guide shaft 100, like shown in the embodiment in FIG. 2, and the holder having couple means in the form of lever arm 42 and of sphere 44, which can be brought in engagement with working instrument 24, so that, in a relative movement between working instrument 24 and guide shaft 100, holder 101 is pivoted in order to track optical axis 30 to working area 36, locking means 110 are provided for guide shaft 100 in order to immobilize working instrument 24 at least partially axially relative to guide shaft 100.

Locking means 110 have, according to FIG. 9, at guide shaft 100, preferably in its extracorporal portion, an annular groove 112, in which a pin 114 runs which is provided at working instrument 24. Pin 114 is preferably spring-loaded so that it may be disengaged by means of a suitable snap-lock mechanism not shown with annular groove 112 and can, on its own, snap into annular groove 112. Working instrument 24 remains freely rotatable about its longitudinal axis by locking means 110 in guide shaft 100.

While, by a rotation of working instrument 24 about its longitudinal axis, guide shaft 100 is, thus, not rotated, and the adjusted viewing direction of image pick-up unit 20 is, thus, not changed, guide shaft 100 is entrained into the same direction by an axial movement of working instrument 24, and via the mechanical coupling of image pick-up unit 20 via pivot arm 104 at guide shaft 100, same is parallely moved in the same way. In a rotation of working instrument 24 about its longitudinal axis, image pick-up unit 20 remains unchanged in its position.

Locking means 110 causes, thus, a complete axial fixation of working instrument 24 with respect to guide shaft 100.

In comparison, in FIG. 10, a modified embodiment of locking means 110' is shown, which are configured in such a way that working instrument 24 is axially displaceable relative to guide shaft 100 within predetermined limits, but entrains guide shaft 100 when the displacement exceeds the predetermined axial limits.

To this end, locking means 110' are configured with an annular groove 112' at guide shaft 100 and a pin 114' at working instrument 24 in a manner comparable to FIG. 9, with pin 114' being axially shorter than annular groove 112'.

Working instrument 24 can be, thus, be axially displaced over a distance relative to guide shaft 100, which corresponds to the difference of the axial length of annular groove 112' and the axial length of pin 114'. The limits mentioned before of the axial free mobility are, thus, determined by the front end 116 and the rear end 118 of annular groove 112' and by the axial length of pin 114'.

Within this free axial mobility of working instrument 24 relative to guide shaft 100, when working instrument 24 is displaced, guide shaft 100 is, thus, not also displaced, whereby, correspondingly, image pick-up unit 20 also is not moved and, thus, the viewing direction of optical axis 30 is maintained. The point of working instrument 24 can, thus, be moved within the predetermined limits in the unchanged image field. The limits mentioned before of the relative mobility between working instrument 24 and guide shaft 100 are, advantageously, adjusted in such a way that the range of the free axial mobility corresponds exactly to the distance between the entering in and the outgoing of the point of working instrument 24 out of the image field. Only if the point of working instrument 24 would leave the image field, guide shaft 100 and, thus, image pick-up system 20 would also be moved.

What is claimed is:

1. A device for intracorporal, minimal-invasive treatment of a patient, comprising:
    a working instrument that can be introduced into a body cavity of said patient for carrying out a treatment step, said working instrument having a distal end defining an intracorporal working area when said working instrument is introduced in said body cavity;
    at least one image pick-up unit for picking up an image of said intracorporal working area, said image pick-up unit having an optical axis; and
    positioning means for orienting said optical axis of said image pick-up unit in dependency on a spatial position of said intracorporal working area, said positioning means further comprising:
        a guide shaft in which said working instrument is guided, said guide shaft having an intracorporal portion, and
        a holder pivotably fixed to said intracorporal portion of said guide shaft, wherein said image pick-up unit is arranged at said holder at a distance from a location where said holder is linked to said guide shaft, such that said image pick-up unit is intracorporally pivotable into a working position, in which said optical axis runs angularly to a longitudinal center axis of said guide shaft and points to said longitudinal center axis.

2. The device of claim 1, wherein said holder has at least one pivot arm that is articulatedly fixed to said intracorporal portion.

3. The device of claim 2, wherein said image pick-up unit is arranged at a free end of said at least one pivot arm in such a way that said optical axis of said image pick-up unit runs approximately perpendicular to a longitudinal axis of said pivot arm and points to said longitudinal canter axis of said guide shaft.

4. The device of claim 3, wherein said pivot arm has an adjustable length.

5. The device of claim 1, wherein said holder has a multi-axis articulation mechanism.

6. The device of claim 1, wherein said image pick-up unit is pivotable into a resting position at said guide shaft, in which an outer cross-sectional contour of said image pick-up unit is arranged in an essentially congruent manner with respect to an outer cross-sectional contour of said guide shaft.

7. The device of claim 1, wherein said image pick-up unit is fixable via an intracorporally activatable coupling mechanism at said guide shaft.

8. The device of claim 1, wherein said positioning means comprise a mechanically constrained coupling between said working instrument and said image pick-up unit.

9. The device of claim 8, wherein said positioning means have locking means for an at least partial axial immobilization of said working instrument with respect to said guide shaft.

10. The device of claim 9, wherein said locking means are configured in such a way that said working instrument is axially freely displaceable with respect to said guide shaft within predetermined limits, but axially entrains said guide shaft, if said working instrument is displacecd beyond said predetermined axial limits.

11. The device of claim 1, wherein said positioning means comprise a mechanically constrained coupling between said working instrument and said image pick-up unit, and wherein said working instrument is axially freely displaceable with respect to said guide shaft, and wherein said holder has coupling means, which can be brought in engagement with said working instrument in such a way that, when said working instrument is displaced relative to said guide shaft, said holder is pivoted, in order to track said optical axis to said working area.

12. The device of claim 1, wherein said positioning means comprise an actuator unit for pivoting said image pick-up unit and a sensor unit coupled therewith, by which a current position of said working area can be determined.

13. The device of claim 12, wherein said sensor unit comprises measuring means for determining a relative position of said working instrument with reference to said guide shaft.

14. The device of claim 1, wherein said positioning means comprise an actuator unit for pivoting said image pick-up unit and a sensor unit coupled therewith, by which a current position of said working area can be determined, and wherein said sensor unit comprises image processing means for identification of said distal end of said working instrument in said image picked up.

15. The device of claim 1, wherein, in the working position, said optical axis encloses an angle of at least 10°, with said longitudinal center axis of said guide shaft.

16. The device of claim 15, wherein, in the working position, said optical axis encloses an angle of between 20° and 70 with said longitudinal center axis of said guide shaft.

17. The device of claim 1, wherein, in the working position, an image entrance opening of said image pick-up unit is in a lateral distance from said guide shaft, which is larger than approximately 1 cm.

18. The device of claim 1, wherein said image pick-up unit is a video probe, which provides an electrical image signal of said working area.

19. The device of claim 18, wherein said image picked up by said image pick-up unit is telemetrically transmitted.

20. The device of claim 19, wherein said image pick-up unit has a transmitter, transmitted image signals of which are received by a receiver.

21. The device of claim 20, wherein said receiver or at least its antenna is arranged at said intracorporal portion of said guide shaft.

22. The device of claim 1, wherein an illuminating device is arranged at said image pick-up unit, which has preferably at least one light emitting diode.

23. The device of claim 1, wherein said image pick-up unit has a source of energy for its supply.

24. The device of claim 1, wherein said image pick-up unit is an optical element, which provides an optical image signal of said working area.

25. The device of claim 1, wherein said guide shaft has a guide channel that is open on both ends for receiving and guiding exchangeable working instruments.

26. The device of claim 1, wherein said working instrument is immovable in radial direction in said guide shaft.

27. The device of claim 1, wherein said working instrument is freely rotatable about its longitudinal axis in said guide shaft.

28. The device of claim 1, wherein said image pick-up unit has means for modification of a picked up image sector.

29. The device of claim 1, wherein an illuminating device is arranged on said intracorporal portion of said guide shaft.

* * * * *